United States Patent [19]

Lam

[11] 4,340,733

[45] Jul. 20, 1982

[54] PROCESS FOR PREPARING 3-CHLORO-6-(2-HYDROXYPHENYL)-PYRIDAZINES

[75] Inventor: Bing L. Lam, King of Prussia, Pa.

[73] Assignee: SmithKline Corporation, Philadelphia, Pa.

[21] Appl. No.: 182,913

[22] Filed: Sep. 2, 1980

[51] Int. Cl.$^3$ .......................................... C07D 237/12
[52] U.S. Cl. ................................................... 544/224
[58] Field of Search ........................................ 544/224

[56] References Cited

U.S. PATENT DOCUMENTS 4,053,601 10/1977 Coates et al.
4,111,935 9/1978 Coates et al.

OTHER PUBLICATIONS

Derwent Abstract 30597B (Japanese 5 4032-489).
Aki et al., *Chem. Pharm. Bull.* 20(6):1325–1327 (1972).
Schulte et al., *Angew. Chem. Intern. Edit.* 4:1081–1082 (1965).
Kallury et al., Tetrahedron Letters No. 41, 3655–3658 (1977).

*Primary Examiner*—Mark L. Berch
*Attorney, Agent, or Firm*—Joan S. Keps; Richard D. Foggio; Alan D. Lourie

[57] ABSTRACT

A process for preparing 3-chloro-6-(2-hydroxyphenyl)-pyridazines by the reaction of 6-(2-hydroxyphenyl)-3(2H)-pyridazinones with phosphorus oxychloride and a disubstituted formamide. The chloropyridazine compounds are useful intermediates for preparing compounds which have β-adrenergic blocking and vasodilator activity and are useful as antihypertensive agents.

3 Claims, No Drawings

PROCESS FOR PREPARING 3-CHLORO-6-(2-HYDROXYPHENYL)-PYRIDAZINES

This invention relates to a new process for preparing 3-chloro-6-(2-hydroxyphenyl)pyridazines which are useful intermediates for the preparation of 3-[2-(3-substituted amino-2-hydroxypropoxy)phenyl]-6-hydrazinopyridazine compounds having β-adrenergic blocking and vasodilator activity and being useful as antihypertensive agents (U.S. Pat. No. 4,053,601).

The conversion of a 6-(2-hydroxyphenyl)-3(2H)-pyridazinone to a 3-chloro-6-(2-hydroxyphenyl)pyridazine by a series of reactions, i.e. protecting the phenolic hydroxy group, treating with phosphorus oxychloride and then deprotecting the protected phenolic hydroxy, is known (U.S. Pat. No. 4,111,935). The present invention provides a method of converting a 6-(2-hydroxyphenyl)-3(2H)-pyridazinone to a 3-chloro-6-(2-hydroxyphenyl)pyridazine in one step. The phenolic hydroxy group does not require protection during the process of this invention.

According to the process of this invention, a 6-(2-hydroxyphenyl)-3(2H)-pyridazinone is reacted with phosphorus oxychloride and a disubstituted formamide to give a 3-chloro-6-(2-hydroxyphenyl)pyridazine.

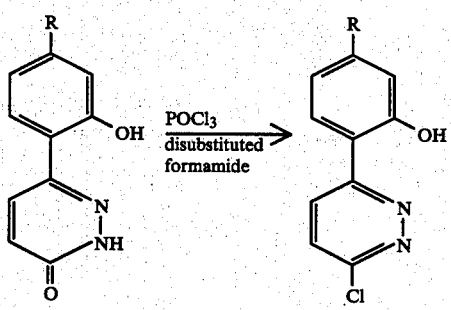

The term R is hydrogen or lower alkyl.

It is known to use phosphorus oxychloride and a disubstituted formamide to achieve formylation; the reaction is known as the Vilsmeier-Haack reaction and the combination of agents is called the Vilsmeier reagent. It has been reported that heterocycles having a keto group adjacent to a ring nitrogen, are chloroformylated by treatment with phosphorus oxychloride and dimethylformamide to give the 2-chloro-3-formyl derivatives. Aki et al., *Chem. Pharm. Bull.* 20(6):1325–1327 (1972) prepared 2-chloro-3-formyl compounds from a benzazepin-2-one and thiazin-3-ones. Also, 2-chloro-3-formylpyrroles were prepared from α-pyrrolones by the Vilsmeier-Haack reaction by Schulte et al., *Angew. Chem. Intern. Edit.* 4:1081–1082 (1965).

When the pyridazin-3-one is reacted with phosphorus oxychloride and a disubstituted formamide according to the process of the invention, the keto group is converted to chloro but no formylation occurs. Thus, the Vilsmeier reagent acts in this process as a chlorinating agent.

In the process of this invention, the disubstituted formamide is preferably a dilower alkylformamide, most preferably dimethylformamide. Other disubstituted formamides for example diphenylformamide or N-methyl-N-phenylformamide may also be used.

Preferably, in the present process, the 6-(2-hydroxyphenyl)-3(2H)-pyridazinone is added to a cold mixture of phosphorus oxychloride and the disubstituted formamide. The reaction mixture is then heated to about 75°–90° C. for about 4–5 hours. The product is isolated from the reaction mixture by methods known to the art for example by cooling the reaction mixture, quenching in cold water, preferably below 40° C., and filtering to give the 3-chloro-6-(2-hydroxyphenyl)pyridazine.

3-Chloro-6-(2-hydroxyphenyl)pyridazines are useful as intermediates for the production of pharmacologically active compounds, in particular 3-[2-(3-substituted amino-2-hydroxypropoxy)phenyl]-6-hydrazinopyridazines which have β-adrenergic blocking and vasodilator activity and are useful as antihypertensive agents. These hydrazinopyridazines are described in U.S. Pat. No. 4,053,601.

The 3-chloro-6-(2-hydroxyphenyl)pyridazines can be converted into a 3-[2-(3-substituted amino-2-hydroxypropoxy)phenyl]-6-hydrazinopyridazines by successive reaction with an epihalohydrin, a substituted amine such as t-butylamine, and hydrazine or by successive reaction with hydrazine, protection of the hydrazino group, reaction with an epihalohydrin and a substituted amine, such as t-butylamine, and removal of the hydrazino protecting group.

The invention is illustrated but not limited by the following examples. The temperatures are in degrees Centigrade.

EXAMPLE 1

Dimethylformamide (85 ml.) was cooled to 5° and phosphorus oxychloride (115 ml.) was added slowly to maintain a solution temperature below 60°. 6-(2-Hydroxyphenyl)-3(2H)-pyridazinone (30 g., 0.16 m.) was added rapidly in several portions. The reaction mixture was heated to 85° and held at this temperature for 4.5 hours with stirring. The mixture was then cooled to 35° and poured into 1 liter of ice cold water keeping the quenched solution below 35°. The resulting precipitate was filtered off, washed with water and dried to give 30.8 g. (96% yield) of crude 3-chloro-6-(2-hydroxyphenyl)pyridazine.

The crude product was continuously extracted with 350 ml. of ethyl acetate in an extractor for 1.5 hours. The resulting product was precipitated from the ethyl acetate solution upon cooling. A second crop was obtained upon concentration of the filtrate. Upon workup, 21.5 g. of 3-chloro-6-(2-hydroxyphenyl)pyridazine was obtained.

Alternatively, the crude product may be purified by the following procedure. One hundred grams of the crude product was dissolved in 250 ml. of hot dimethylformamide (100°). Warm (60°) isopropanol (200 ml.) was added with mixing. The mixture was allowed to cool to 10°. The crystallized 3-chloro-6-(2-hydroxyphenyl)pyridazine was filtered and washed with 2-propanol. Dried weight was 80 g. (80% yield from crude product).

EXAMPLE 2

By the procedure of Example 1, using 6-(2-hydroxy-4-methylphenyl)-3(2H)-pyridazinone in place of 6-(2-hydroxyphenyl)-3(2H)-pyridazinone, 3-chloro-6-(2-hydroxy-4-methylphenyl)pyridazine is obtained.

EXAMPLE 3

A mixture of 3-chloro-6-(2-hydroxyphenyl)pyridazine (2.69 g.), epibromohydrin (4.5 ml.), anhydrous potassium carbonate (3.6 g.) and dry butane-2-one (100 ml.) was stirred and heated under reflux for 16 hours. The mixture was filtered and the filtrate was evaporated to dryness and the residue was twice recrystallized from ethanol to give 3-chloro-6-(2-epoxypropoxyphenyl)pyridazine, m.p. 118°–119°.

A mixture of 3-chloro-6-(2-epoxypropoxyphenyl)pyridazine (0.7 g.), methanol (7 ml.) and t-butylamine (1.7 ml.) was stirred and heated under reflux for 1.25 hours. The mixture was evaporated under reduced pressure at 50° and the residue was recrystallized from toluene to give 3-chloro-6-[2-(3-t-butylamino-2-hydroxypropoxy)phenyl]pyridazine, m.p. 136.5°–137.5°. A sample of this product was treated with hydrochloric acid (1.0 N, 3.62 ml.), the solution was extracted with dichloromethane and the aqueous solution was evaporated under reduced pressure and the residue was recrystallized from ethanol/ether to give the monohydrochloride salt, m.p. 193.5°–194.5°.

A stirred mixture of 3-chloro-6-[2-(3-t-butylamino-2-hydroxypropoxy)phenyl]pyridazine hydrochloride (0.3 g.) and hydrazine hydrate (3 ml.) was heated under reflux for 50 minutes. After cooling, dichloromethane was added and this mixture was extracted with water, the dichloromethane was removed by evaporation and the residue was treated with a mixture of n-propanol (1.2 ml.) and concentrated hydrochloric acid (0.13 ml.) to give 3-[2-(3-t-butylamino-2-hydroxypropoxy)phenyl]-6-hydrazinopyridazine dihydrochloride, m.p. 163°–168°.

What is claimed is:

1. A process for preparing a pyridazine compound of the formula:

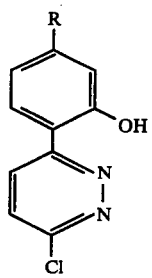

in which R is hydrogen or lower alkyl, which comprises reacting a pyridazinone of the formula:

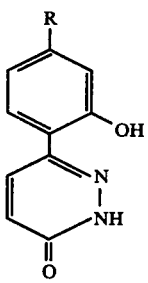

with phosphorus oxychloride and a dilower alkylformamide.

2. A process according to claim 1 in which the dilower alkylformamide is dimethylformamide.

3. A process according to claim 1 in which the reaction is carried out at about 75°–90° C.

* * * * *